United States Patent [19]

Malmin

[11] 4,346,713
[45] Aug. 31, 1982

[54] HAIR REPLACEMENT METHOD

[76] Inventor: Oscar Malmin, 127 E. Wayne Ave., Akron, Ohio 44301

[21] Appl. No.: 935,521

[22] Filed: Aug. 21, 1978

Related U.S. Application Data

[63] Continuation-in-part of Ser. No. 876,482, Feb. 9, 1978, abandoned, which is a continuation-in-part of Ser. No. 855,272, Nov. 28, 1977, abandoned.

[51] Int. Cl.³ ............................................. A61B 17/00
[52] U.S. Cl. .................................................... 128/330
[58] Field of Search ................... 128/330, 329 R, 1 R, 128/335.5; 3/1; 46/172; 132/53, 56, 5

[56] References Cited

U.S. PATENT DOCUMENTS

| | | | |
|---|---|---|---|
| 1,059,631 | 4/1913 | Popovics | 128/330 |
| 2,253,635 | 8/1941 | Mann | 46/172 |
| 2,636,460 | 4/1953 | Seiderman | 112/1 |
| 3,062,214 | 11/1962 | Maxwell | 128/330 |
| 3,119,398 | 1/1964 | Bennett et al. | 128/330 |
| 3,421,521 | 1/1969 | Rich | 132/5 |
| 3,513,860 | 5/1970 | Kost | 132/5 |
| 3,553,737 | 1/1971 | Bauman | 3/1 |
| 3,589,376 | 6/1971 | Kohler | 132/5 |
| 3,596,292 | 8/1971 | Erb | 3/1 |
| 3,608,095 | 9/1971 | Barry | 3/1 |
| 3,699,969 | 10/1972 | Allen | 128/330 |
| 3,755,824 | 9/1973 | Sperling | 3/1 |
| 3,845,772 | 11/1974 | Smith | 128/335 |
| 3,858,245 | 1/1975 | Nate et al. | 3/1 |
| 3,877,570 | 4/1975 | Barry | 206/63.3 |
| 3,908,674 | 9/1975 | Kessler | 132/53 |
| 3,914,801 | 10/1975 | Dick et al. | 3/1 |
| 4,027,675 | 6/1977 | Colone | 128/330 |
| 4,054,954 | 10/1977 | Makayama et al. | 128/330 X |
| 4,057,535 | 11/1977 | Lipatova et al. | 128/335.5 X |
| 4,103,365 | 8/1978 | Applegate | 128/330 X |

FOREIGN PATENT DOCUMENTS 30751 5/1920 Norway .............................. 128/330

Primary Examiner—Michael H. Thaler
Attorney, Agent, or Firm—Reese Taylor

[57] ABSTRACT

A method of treating baldness by inserting strands of natural or synthetic hair into the scalp by suitable penetration means is disclosed. The method essentially involves passing a U-shaped loop of hair through the tissue beneath the scalp so that the base of the U protrudes therefrom and engaging the base of a second U-shaped strand with the first strand following which the first strand is pulled in the reverse direction so that the interengaged portions are disposed beneath the scalp in the insertion pathway. The method also includes the alternative of performing a unit of two interlocking strands whose true ends have been joined chemically, thermally, mechanically or electronically and inserting the units beneath the scalp with their opposed ends projecting from the penetration openings. The methods further contemplate applying a biodegradable tissue adhesive or tissue inert material at the point of interconnection of the strands or to join the free ends of the units and further contemplates the possible steps of applying similar material adjacent the perforation points where the strands were inserted into the scalp. Suitable apparatus such as skewers having various strand carrying pockets and various configurations are also disclosed to implement the method.

4 Claims, 35 Drawing Figures

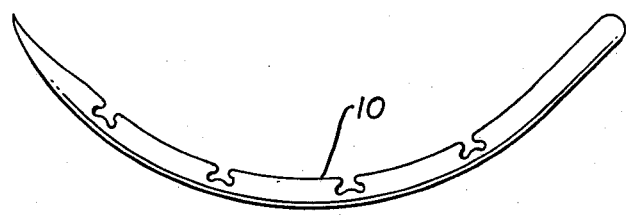
FIG. 7
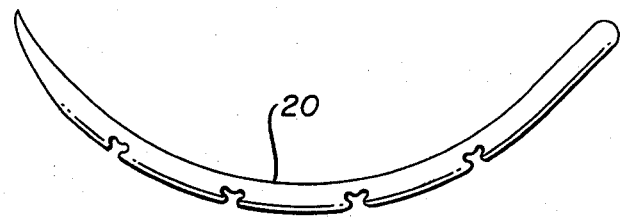
FIG. 8
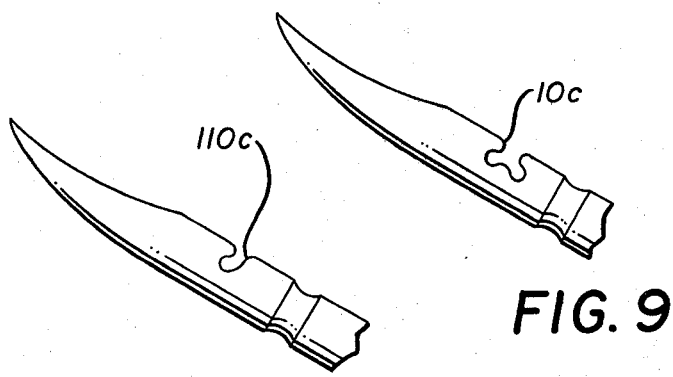
FIG. 9
FIG. 10
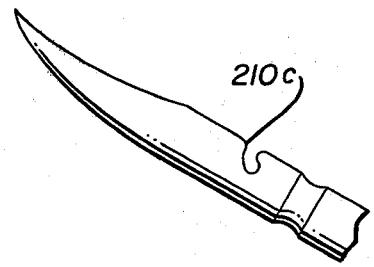
FIG. 11
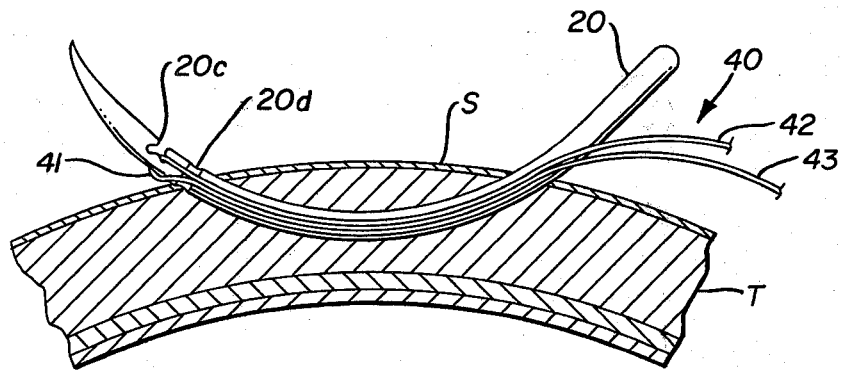
FIG. 12

HAIR REPLACEMENT METHOD

RELATED APPLICATIONS

This application is a continuation-in-part of applicant's earlier filed application Ser. No. 876,482 filed Feb. 9, 1978, for "Hair Replacement Method and Apparatus" now abandoned which was a continuation-in-part of applicant's earlier filed application Ser. No. 855,272 filed Nov. 28, 1977, for "Hair Replacement Method and Apparatus", now abandoned.

BACKGROUND OF THE INVENTION

This invention relates, in general, to the treatment of baldness and relates in particular to a method of treating baldness by inserting strands of synthetic fiber or natural hair beneath the surface of the scalp with their free ends protruding in such a manner that the strands are mechanically, thermally, chemically or electronically interlocked with each other to insure retention and also to a method of assisting retention beneath the scalp by the cellular adaption of natural healing between and around the strands and their interengaging points.

PRIOR ART STATEMENT

There are a number of known treatments and methods of correcting baldness but problems with poor appearance and anchoring have been encountered. In general, hairpieces have long been known as one method of solving the problem of baldness.

Other methods have involved implanting various retaining devices such as, for example, specially treated wires or sutures into the scalp with portions thereof being exposed and with the exposed portions forming a network to which strands of natural or synthetic hair can be tied or woven. Difficulties have developed with these methods however with regard to infection and also to the requirement for periodic tightening or reweaving.

Still further methods have involved cutting a circular plug containing hair follicles from a donor site and transplanting that plug into a prepared recipient site in the bald area. There is a high rate of rejection with this method however.

Still further methods have involves the general concept of embedding synthetic fibers or natural hair into the scalp but a severe problem with regard to anchoring the fibers has been encountered leading to a high failure rate which is believed to be caused by an inability to resist the healing forces for any reasonably long period or of secondary infection, with a consequent expulsion or rejection of the embedded hair.

With regard to the patent prior art there are a large number of patents in existence and known to applicant relating to this general field many of which reflect various of the aforementioned methods.

Bauman U.S. Pat. No. 3,553,737 illustrates one of the "weaving" methods and discloses one of the methods above referred to wherein an anchor member, in the form of a continuous suture, is embedded into the scalp to which a web is attached following which the hair can be attached to the web.

Barry U.S. Pat. No. 3,608,095 is illustrative of the "hairpiece" methods discloses the placing of loops in the scalp to which a hairpiece can be attached.

Allen U.S. Pat. No. 3,699,969 discloses a hair implant method of one of the types generally referred to above wherein a plug of natural or synthetic fibers is inserted directly into the scalp by means of a concentric dual needle arrangement relying, however, on acceptance of the implanted plug.

Nate U.S. Pat. No. 3,858,245 discloses the utilization of individual suture loops which are sewn into the scalp and serve as anchors for attaching wefts of hair similar to Bauman.

Dick U.S. Pat. No. 3,914,801 also discloses forming suture loops in concentric circles on the scalp following which wefts of hair may be attached thereto.

Colone U.S. Pat. No. 4,027,675 discloses the implanting of loops of hair into the subcutaneous portion of the head with the ends of adjacent loops being tied together. However, these points of interconnection are external and would present obvious problems in grooming the hair.

Erb U.S. Pat. No. 3,596,292 discloses a hair implant method where the implanted hair has a percutaneous portion having elastic properties and a divergent cross-section for anchoring purposes.

Bennett U.S. Pat. No. 3,119,398 also discloses an implanting method wherein single strands of hair are processed so as to provide a nearly natural root structure to again assist in anchoring.

Popovics U.S. Pat. No. 1,059,631 primarily discloses an instrument for implanting hairs directly into the scalp.

Maxwell U.S. Pat. No. 3,062,214 also discloses apparatus for implanting the fibers, and particularly the ends thereof, directly into the scalp.

Barry U.S. Pat. No. 3,877,570 is another of the "hairpiece" approaches and discloses a sterile suture suitable for attaching hairpieces to the scalp.

Kost U.S. Pat. No. 3,513,860 discloses another method in which the hair is formed into U-shaped loops and the bases of the loops are pushed into the scalp. The reference however fails to disclose the interengagement of a plurality of looped strands of hair which is one of the objects of the present invention.

Smith U.S. Pat. No. 3,845,772 discloses a retention suture which possibly could be utilized in connection with treating baldness but is silent with regard to anchoring the actual strands beneath the scalp.

Kessler U.S. Pat. No. 3,908,674 discloses a method of securing hairpieces to cover a bald area of the scalp wherein sutures are permanently implanted within the scalp and the hairpiece is secured thereto.

Sperling U.S. Pat. No. 3,755,824 discloses another method for avoiding the appearance of baldness wherein sutures are located permanently at strategic locations on the scalp and a scalp net is secured thereto.

Kohler U.S. Pat. No. 3,589,376 is essentially directed to a method of making wigs.

Rich U.S. Pat. No. 3,421,521 is also directed to a method of forming a hairpiece per se as is Mann U.S. Pat. No. 2,253,635.

Seiderman U.S. Pat. No. 2,636,460 discloses a process for manufacturing products simulating human or animal hair and its only pertinency is the fact that loops are inserted into the base or scalp portion of the head.

Norwegian Pat. No. 30,751 is of some interest also in that two hairs are joined together at their root ends by a gold wire. However there is no teaching of the use in interlocked loops of hair.

Nakayama U.S. Pat. No. 4,054,954 is also of interest in showing an endless suture which is embedded under the scalp and a plurality of rings threaded onto the suture which serve as anchoring means for a hairpiece.

While this patent art is illustrative of the several known methods of treating baldness none of it, however, discloses the unique method disclosed by applicant wherein both a mechanical and a natural interlocking are achieved by utilizing interconnected U-shaped strands of hair and wherein retention of the strands is assisted by both mechanical and chemical means.

SUMMARY OF THE INVENTION

It has been found that many of the disadvantages of the prior art can be eliminated by a relatively simple yet effective method of treating baldness.

It is a general object of this invention to provide a method of treating baldness wherein various penetration members such as skewers are employed to puncture the scalp forming a passageway therein and to insert paris of chemically, mechanically, thermally or electronically interengaged fibers in the passageway with their free ends projecting from the penetration points in the scalp.

In one form it is an object of this invention to provide a method of treatment wherein the various skewer devices are employed to puncture the scalp forming a passageway for insertion of the first strand of hair, in the form of a U-shaped loop, into the tissue beneath the scalp with the base of the U-shaped loop projecting therefrom. Following this, a second similar strand may be engaged with and attached to the loop of the first and, optionally, a biodegradable tissue adhesive can be applied at the point of interconnection.

The interconnection between the strands may be made by either engaging the bases of the U-shaped loops or by tying one loop to the other.

The first strand may then be drawn back beneath the surface of the scalp in the reverse direction so that the mechanical interconnection between the two loops is disposed beneath the surface of the scalp with the free ends of the two strands projecting therefrom and forming the surface hair.

In another form it is an object of the invention to actually join the two strands into a "unit" prior to insertion by the use of thermal, mechanical, chemical or electronic means and similarly joining their free ends following which they can be inserted into the passageway with their opposed ends projecting above the scalp. The previously joined free ends can then be severed so that the projecting ends will simulate natural hair.

In either form the inserted strands can be drawn into place beneath the surface of the scalp so as to place the interengaged portions in the deepest or base portion of the skewer-created pathway.

No matter how the strands are interengaged, if one or both should break they can be retrieved easily without any surgical process.

It is further contemplated that the method can be enhanced by treating the puncture sites formed by the skewers with available hemostatic agents to staunch hemorrhage following which the sites can be cleaned with suitable irrigating and cleaning solutions and a suitable biodegradable tissue adhesive material can be applied at the point at which the free ends emerge from the scalp. In this manner the strands of hair will be securely interengaged and will also, by virtue of the cellular activity in the healing process and the retention of the biodegradable tissue adhesives of the tissue and tissue adhesive, be more or less permanently implanted thereby avoiding some of the problems of the prior art wherein anchoring of the implanted hair is a serious problem.

Finally it is contemplated that skewers having certain unique structural characteristics would be employed in carrying out the method.

Accordingly then production of an improved method and apparatus for treating baldness becomes the principal object of this invention with other objects thereof becoming more apparent upon a reading of the following brief specification considered and interpreted in view of the accompanying drawings.

OF THE DRAWINGS

FIGS. 7 and 8 are views similar to FIGS. 1 through 6 showing the skewers with the strand carrying pockets thereof located at various places.

FIGS. 9, 10 and 11 are enlarged views of the operative ends of the skewers showing various configurations of strand carrying pockets.

FIG. 12 is an elevational view partially in section showing application of the first strand in accordance with the method of this invention.

BRIEF DESCRIPTION OF THE PREFERRED EMBODIMENTS

It first should be noted that, in describing that various embodiments of the apparatus and of the method, reference will commonly be made to "strands" and it should be understood that in all instances such reference is intended to cover both natural hair or synthetic fibers and is employed for the sake of brevity.

FIGS. 1 THROUGH 11

Figure 1:
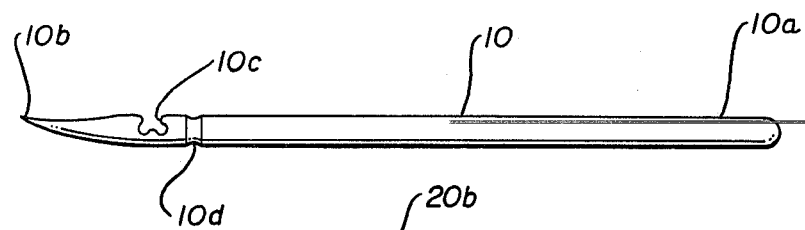
FIG. 1 is a side elevational view of one form of skewer.
Figure 2:
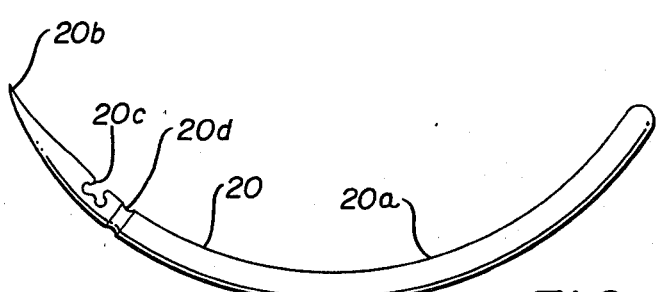
FIG. 2 is a view similar to FIG. 1 showing another configuration of skewer.
Figure 3:
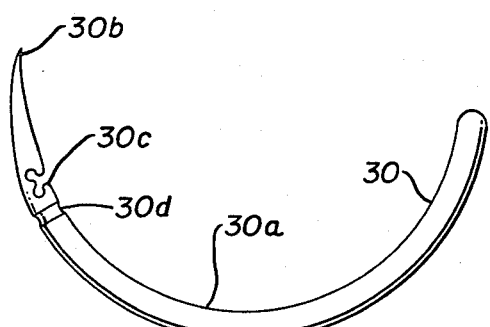
FIG. 3 is a view similar to FIGS. 1 and 2 showing yet another configuration of skewer.

Accordingly then, and turning first to FIGS. 1, 2 and 3 for an examination of some of the skewers employed in carrying out the invention, it will be noted first that in FIG. 1 the skewer 10 has an elongated handle 10a and a sharpened working tip 10b. Disposed inwardly from the tip 10b is a strand carrying pocket 10c. Release means 10d which are annular grooves in the handle 10a are also optionally employed as will be described.

FIGS. 2 and 3 illustrate other configurations of skewers varying from the straight one shown in FIG. 1 to the arcuate configuration of FIG. 2 and the exaggerated arcuate configuration of FIG. 3. Similar reference numbers 10, 20, 30 etc. have been employed in all of these illustrations to designate identical portions of the skewers and they will not be described in detail herein.

Figure 4:
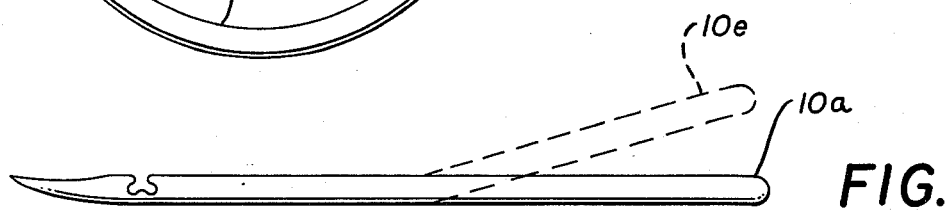
FIGS. 4, 5 and 6 are elevational views showing various still further modified configurations of skewers primarily designed to provide handle or gripping areas for the user.
Figure 5:
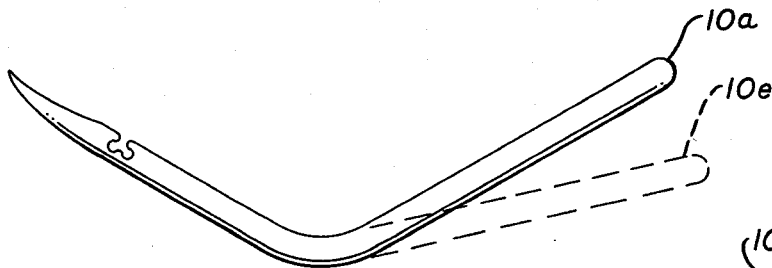
Figure 6:
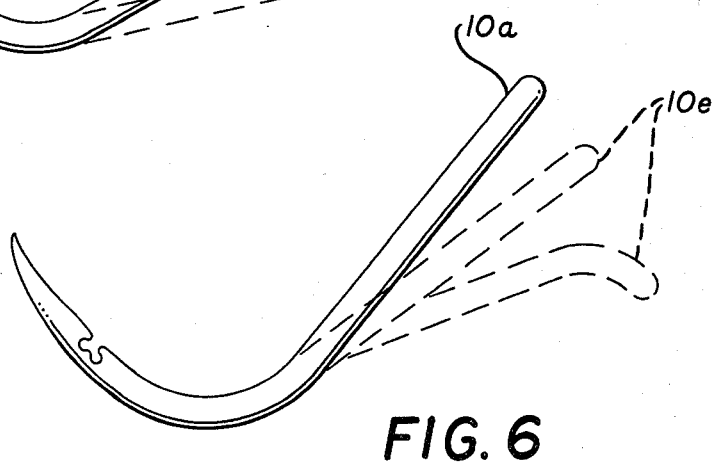

FIGS. 4, 5 and 6 also show variations of the skewers wherein the rear portion of the shank 10a, for example in FIG. 4, is shown in broken lines and distorted form such as at 10e for better gripping purposes. Thus, the skewers could be gripped by hand or by a common holding-inserting device such as a hemostat.

Again similar numbers have been employed in FIGS. 4, 5 and 6 although, since the only essential difference is the actual configuration of the skewer, they will not be described in great detail.

FIGS. 7 and 8 are also similar in showing that the skewers, while taking various configurations, can also have the strand carrying pockets located at various places on the skewer. This, to some extent, is optional and, in fact, a plurality of strand carrying pockets can be also produced so that the user may select the one most advantageous to his own technique.

FIGS. 9, 10 and 11, which are partial elevational views, somewhat enlarged, show varying configurations of pockets wherein the pockets can be modified depending upon whether they are intended to carry one strand or more than one strand. Thus single pockets 110c and 210c would carry one strand in one direction while double pocket 10c would be suitable for engaging more than one strand for movement in two directions as will be described.

In general however, with regard to the various forms of skewers illustrated in FIGS. 1 through 11, it should be noted that the point such as 10b, 20b, 30b may be round or triangular in cross-section with the principal requirement being that the point be sharp enough to penetrate the dermis and the subcutaneous layer of tissue. Furthermore the cross-section of the shanks 10a, 20a, 30a are not in any way limited since they could be round, triangular or other geometric form.

FIGS. 12 THROUGH 23

Turning then to FIGS. 12 through 23 for a description of the various methods of the present invention it will first be assumed that the first strand 40 has been bent back on itself to form a loop or in other words to present a generally U-shaped configuration with a base 41 and free ends 42, 43.

Figure 13:
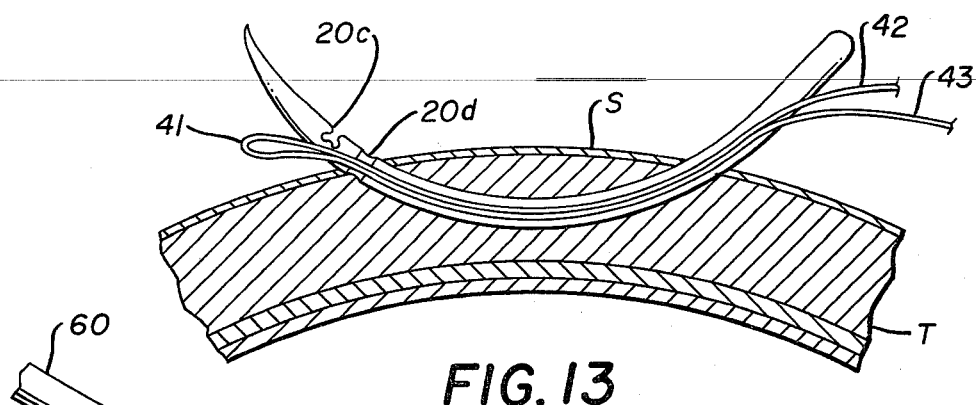
FIG. 13 is a view similar to FIG. 12 showing removal of the first strand from the skewer employed in the step illustrated in FIG. 12.

Following that a skewer such as 20 will have the strand 40 engaged with one side of the engaging notch 20c and the skewer can be passed through the dermis of the scalp S and through the connective tissue or the subcutaneous layer T from right to left of the drawing until the base of the U formed by the strand 40 projects above the surface of the scalp as clearly shown in FIG. 12. It is contemplated that at this point that the strand 40 will be disengaged from the skewer as shown in FIG. 13 by tweezers or other similar instruments.

Here it should be noted that annular recesses 10d, 20d, 30d have been illustrated disposed adjacent notches 10c, 20c, 30c. It has been found that, in some instances, the strands may tend to adhere to the surface of the skewer. Provision of the undercut grooves such as 20d in FIGS. 12 and 13 will provide a space between the surface of the skewer and the strands to further facilitate grasping of the strand for removal. Of course, the reverse construction, or, in other words, a raised ring could also be used for this purpose although it would enlarge the opening caused by the skewer.

Figure 14:
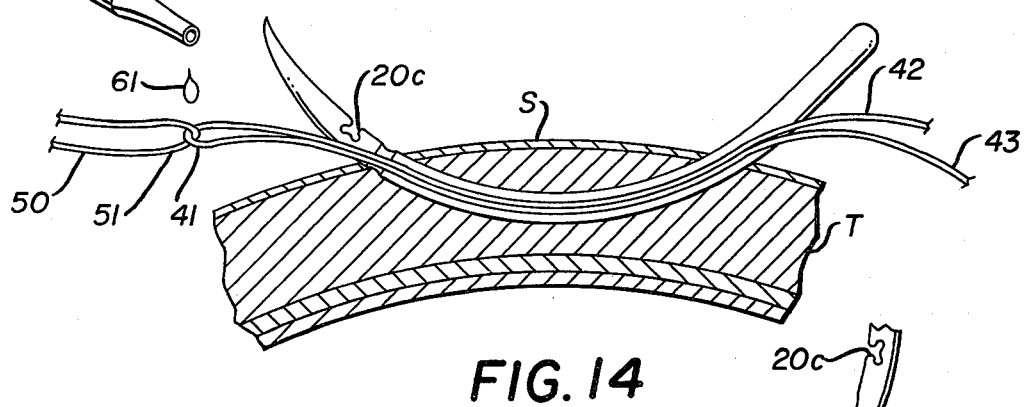
FIG. 14 is a view similar to FIGS. 12 and 13 showing the application of the tissue adhesive material and the interengagement of the second strand.
Figure 15:
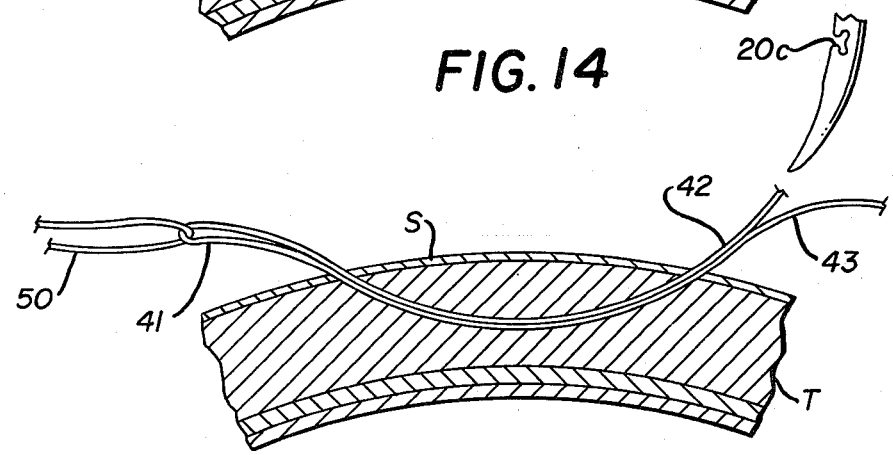
FIG. 15 is a view similar to FIG. 14 showing the skewer removed.

Following placement of first strand 40, as described, a second strand 50 is formed in similar manner and the two loops are interengaged at their bases 41,51 as shown in FIG. 14 of the drawings thereby providing a mechanical interlock between strands 40 and 50.

An optional step takes place at this time. Specifically an applicator 60 is utilized to apply a quantity of tissue adhesive composition composed of a biodegradable material such as isobutyl cyanoacrylate. This will strengthen and stabilize the strands 40 and 50 in the area of the interlock and will also form a nidus for the formation of the blood clotting which precedes the healing process and assist in obtaining a cellular anchorage for the strands.

At this point skewer 20 can be withdrawn to the right (see FIG. 15) although it could also be pulled on through. However, in the event removal of the skewer tends to pull the interengaged strands with it, withdrawal to the right will cause no harm as will be seen.

Figure 16:
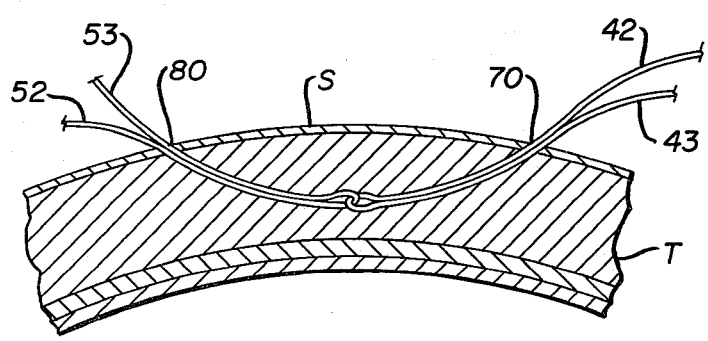
FIG. 16 is a view similar to FIG. 12 showing the two strands in place beneath the surface of the scalp with the skewer removed.
Figure 17:
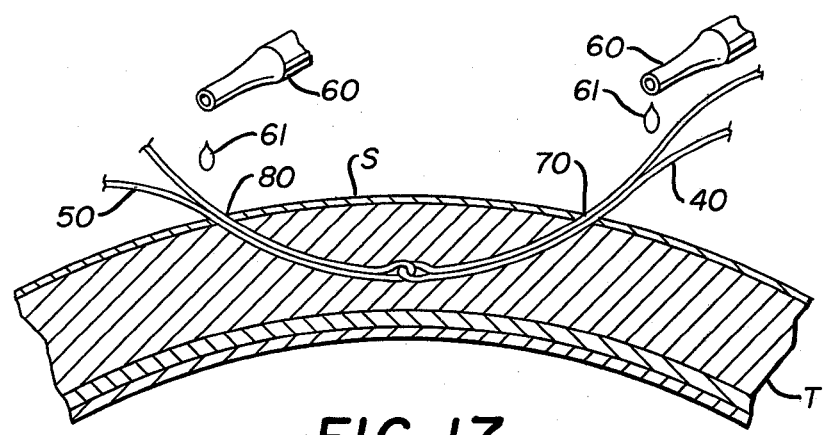
FIG. 17 is view similar to FIG. 12 showing the application of tissue adhesive material to the puncture points formed by the skewer.

Turning next then to FIG. 16, the free ends 42, 43 of the first strand 40 are then grasped by suitable means and pulled back through the channel created by the skewer 20. While the precise final location of the interengaged area of strands 40 and 50 is not absolutely critical, best results are felt to be achieved when this is at approximately midpoint between puncture points 70 and 80. The free ends 42, 43 and 52, 53 of the strands 40 and 50 of course will project above the surface of the scalp S and will constitute the hair which is visible on the head of the patient.

It is also further contemplated, although not illustrated in the drawings, that a hemostatic agent would be employed at the points 70 and 80 of entrance and egress of the skewer to staunch hemorrhaging. The surface of the scalp at this point would then be cleaned with a suitable irrigating and cleansing solution such as, for example, dilute hydrogen peroxide or a sterile saline solution. Following this the biodegradable tissue adhesive material could then again be employed and applied at the puncture points (see FIG. 17).

The process just described could, of course, be repeated the desired number of times until the bald area is covered to suitable density.

It is also anticipated, with reference to FIGS. 18, 19, 20 and 21, that multiple strands may be employed in the same skewer channel. Thus, for example, in FIG. 18 the strands 40 and 50 are illustrated similar to their position in FIG. 14.

Figure 18:
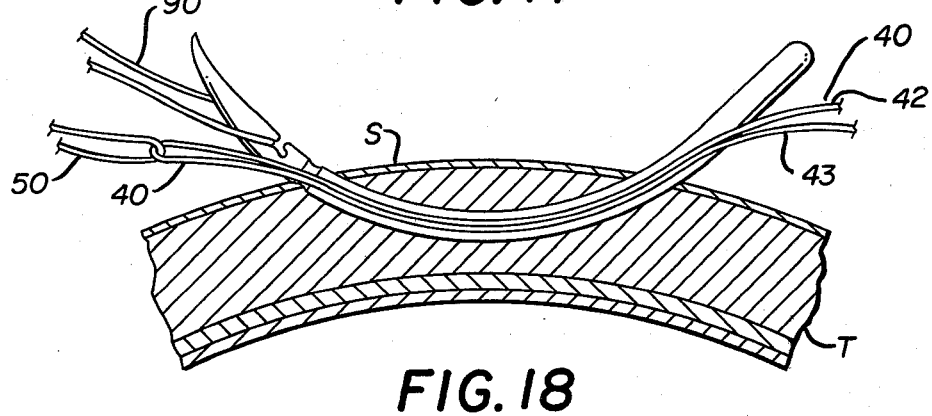
FIG. 18 is a view similar to FIG. 14 showing a third strand engaged with the skewer.
Figure 19:
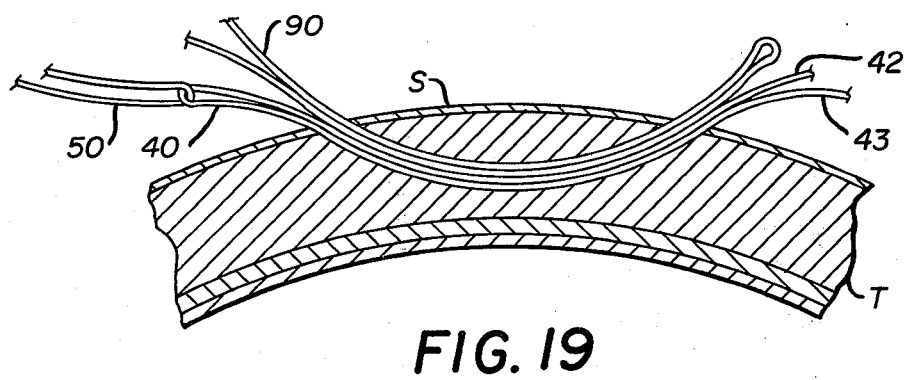
FIG. 19 is a view similar to FIG. 15 showing the third strand in place prior to engagement with a fourth strand.
Figure 20:
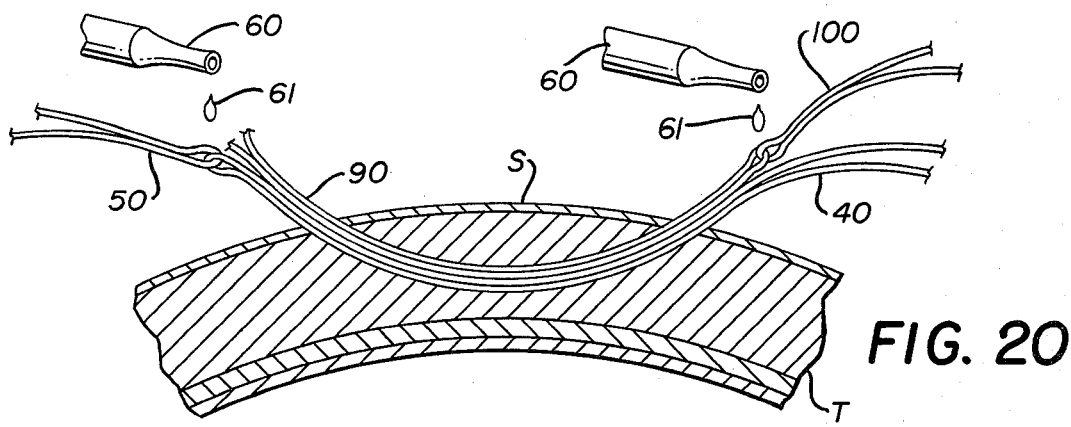
FIG. 20 is a view similar to FIG. 15 showing the third and fourth strands engaged and the application of the tissue adhesive material to the multiple strands.
Figure 21:
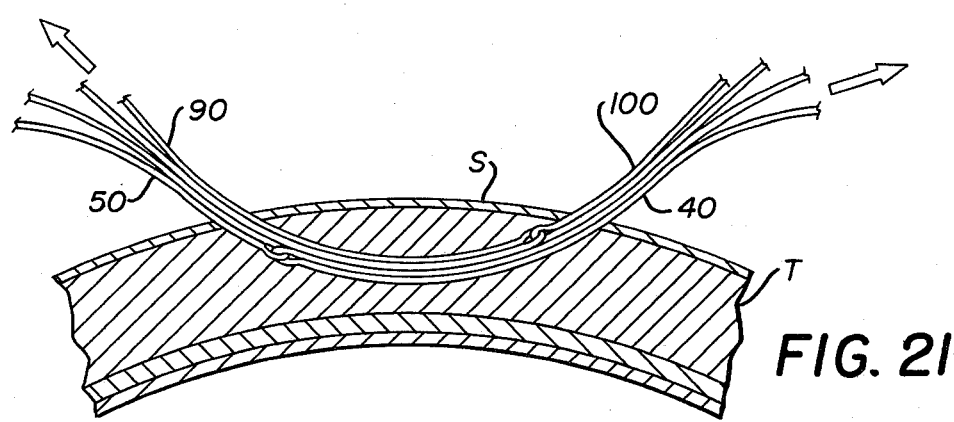
FIGS. 21 and 22 are views similar to FIGS. 15 and 16 illustrating final implacement of the multiple strand arrangement.
Figure 22:
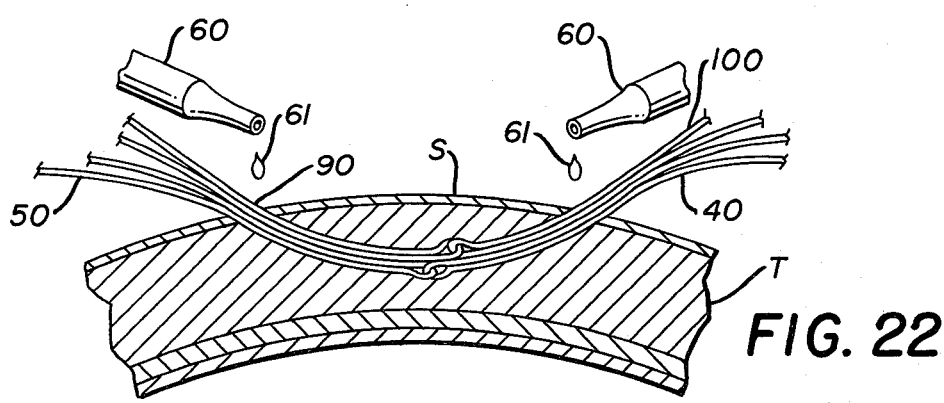

However, with the skewer still in place, a third strand 90 has been engaged with double ended notch 20d as shown in FIG. 18. This strand is then pulled through to the right as shown in FIG. 19 and engaged with strand 100 in the same way strands 40 and 50 are engaged. The tissue adhesive may then be applied and the pairs of strands pulled as shown in FIGS. 21 and 22 following which the tissue adhesive is applied to the puncture points (see FIG. 22).

Thus the skewer 20, with its double ended notch 20d enables the instrument to be employed to implant multiple strands without multiple punctures thereby reducing trauma.

Figure 23:
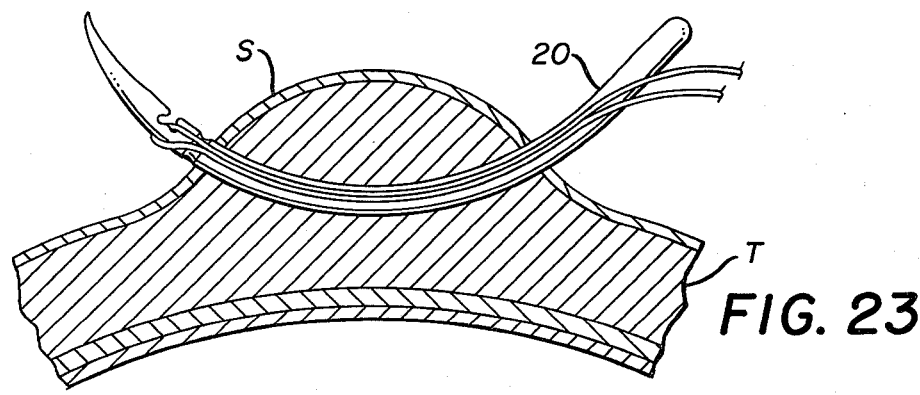
FIG. 23 is a view similar to FIG. 12 wherein the tissue has been raised by compression between the thumb and forefinger or a suitable tissue clamp to further facilitate carrying out of the method.

Finally, FIG. 23 illustrates yet another possible variation in the method in which the tissue is compressed between the thumb and the forefinger or by suitable tissue forceps to present a "bulge" through which the skewer can be passed. The method of operation however is essentially identical.

FIGS. 24 AND 25

Figure 24:
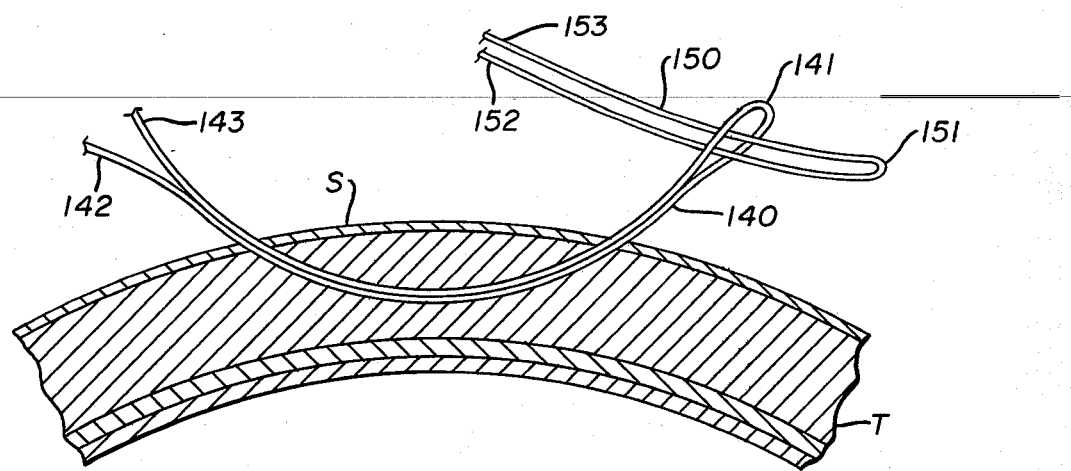
FIG. 24 is a view similar to FIG. 14 showing the first step of a modified method of interengaging the first and second strands.
Figure 25:
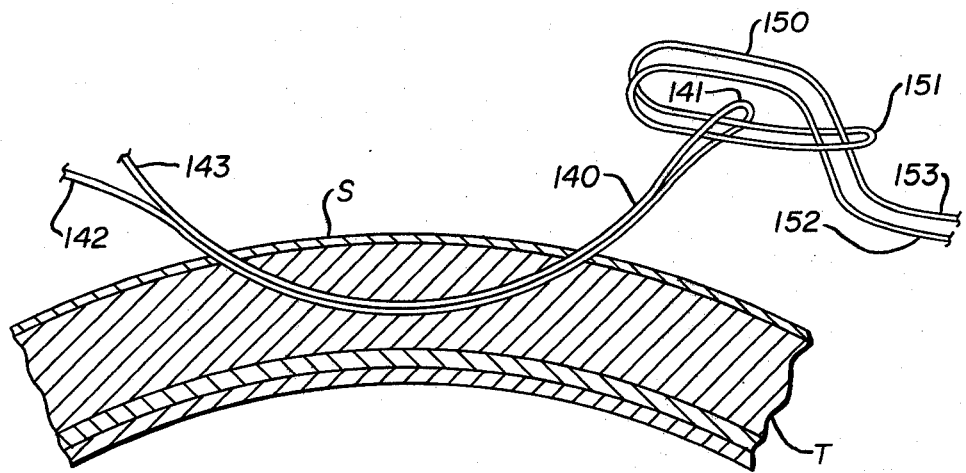
FIG. 25 is a view similar to FIG. 24 showing the second step of the modified method.

Referring to FIGS. 24 and 25 a modified method of interconnecting the strands may be seen. Thus, strand 140 has been passed through the tissue as described above. The second strand 150 then has its base 151 inserted through base 140 of the first strand (FIG. 24). The free ends 152, 153 of second strand 150 are then passed through the base 151 (FIG. 25) to form a knot and interengage the strands. The knot is then drawn tight and the remaining steps are carried out as described above.

FIGS. 26 THROUGH 35

A further modified form of the invention is illustrated in FIGS. 26 through 35.

As noted in the description of the forms of the invention illustrated in FIGS. 12 through 25, essentially the treatment method involves passing a first loop through a passageway formed by the skewer, engaging a second loop to it and pulling the engaged loops back through the passageway in the reverse direction until the point of interengagement is located essentially at the lower most point of the passageway formed by the skewer. These methods permit the "free" ends to be disposed above the level of the scalp and to serve as the simulated hair.

FIGS. 26 through 35 disclose a modification of this broad concept which employs a number of the principles of the other forms of the invention, but permits the preparation of "units" of the strands prior to the actual insertion operation. This could result in increased efficiency and ease of operation as contrasted to attempting to interlock the strands during the actual insertion operation. Furthermore, the interlock or interengagement between the two strands could probably be more precisely governed by machine assembly prior to the operation than by manual means.

Figure 26:
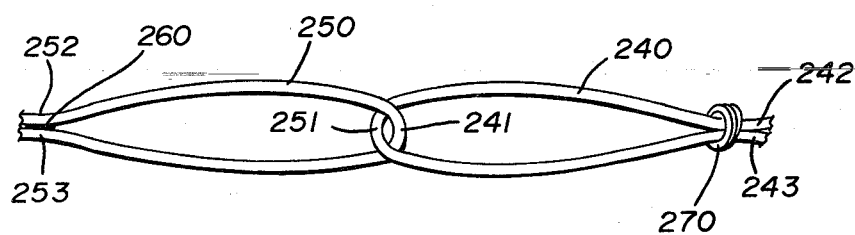
FIG. 26 is a plan view showing the mechanical preengagement of a pair of strands to form a "unit" to be used in a further modified form of the invention.

Accordingly then, reference is first made to FIG. 26 of the drawings which has employed similar numbers for similar compontents. Thus two strands 240 and 250 are employed and are each formed in the shape of a loop. These strands have bases 241,251 and opposed ends 242,243, and 252,253. Essentially, however, as will be noted from FIG. 26, the bases 241,251 have been interlocked and the ends 242,243 and 252,253 have been joined together so that a "unit" is preformed or preassembled.

Still referring to FIG. 26, it will be noted that the numeral 260 indicates joining together of the free ends by a thermal, adhesive or electronic means depending upon the nature of the strand itself. Thus, an adhesive would probably be used if natural hair were employed, while thermal or electronic fusion of the ends could be employed with artificial fibers. Furthermore, it will be noted that a still further method is illustrated in FIG. 26 wherein a tissue inert material 270 is employed to join the ends 242,243 together.

Figure 27:
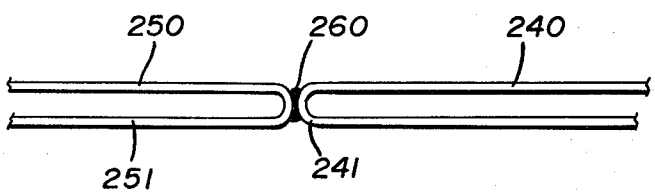
FIG. 27 is a view similar to FIG. 26 showing the chemical, electronic or thermal interengagement of the paired fibers in end-to-end relationship.

FIG. 27 shows a "end-to-end" joining wherein the thermal, adhesive or electronic fusion is illustrated by the numeral 260. It will be understood that in FIG. 27 as well as in FIGS. 28 and 29 the free ends 242,243 and 252,253 are also joined together with these figures merely illustrating possible alternative means of joining the bases 241,251 together to form the "unit".

Figure 28:
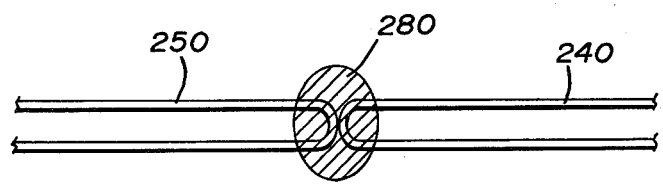
FIG. 28 is a view similar to FIG. 27 showing the interengagement of the fibers using a suitable biodegradeable tissue adhesive.
Figure 29:
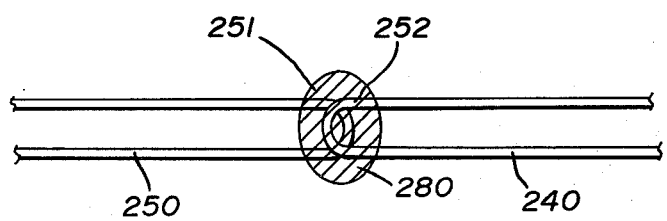
FIG. 29 is a view similar to FIG. 28 showing the overlapping of the bases of the fibers and interengagement by using a suitable biodegradeable tissue adhesive or a tissue inert substance.

In this regard, FIG. 28 illustrates the use of the adhesive 280 while FIG. 29 illustrates the use of adhesive 280 wherein instead of end-to-end relationship between the bases 241 and 251 the same are overlapped.

It should be understood that in carrying out the modified method of the invention described herein, the fibers 240,250 could be secured to each other as desired and that the methods illustrated in FIGS. 26,27,28 and 29 are illustrative only in that they do show alternative ways of prejoining the strands to form a "unit". By the same token the free ends 242,243 and 252,253 are likewise illustrated as being joined in various manners which are alternatives and matters of choice as to which is used without departing from the basic principle of preforming the "unit".

Figure 30:
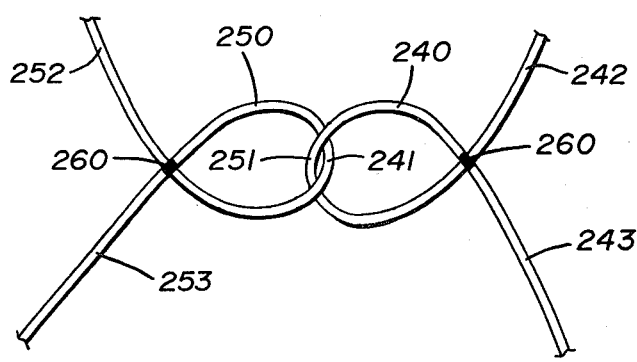
FIG. 30 is a view similar to FIG. 26 showing the formation of full circle first loops by crossing and joining the junction of said crossed fibers after interlocking or otherwise joining each pair of fibers.

FIG. 30, by the same token, is similar to that it shows another alternative method of joining the strands 240 and 250 by forming mechanically interlocked loops and forming full circles and joining the free ends well back from their distal ends by the thermal, adhesive or electronic means 260.

Figure 31:
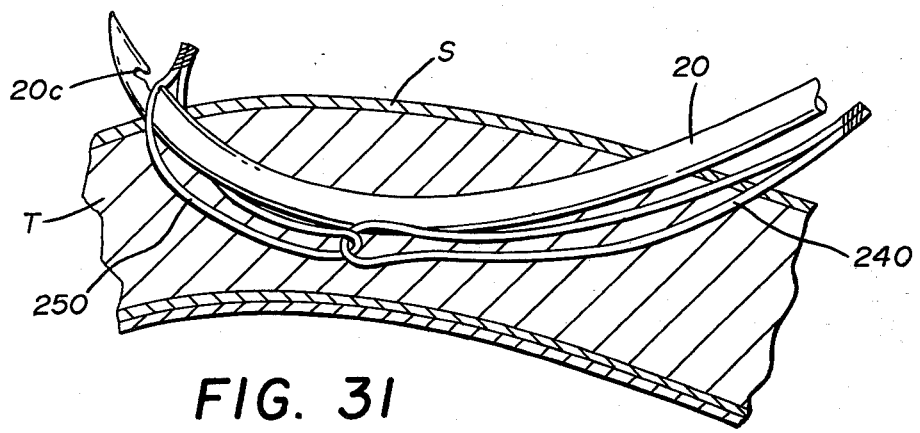
FIG. 31 is a cross-sectional view showing the skewer carrying the preformed unit beneath the scalp with a thrusting action using the forwardly inclined strand or fiber carrying pocket and a second loop of the preformed unit.
Figure 32:
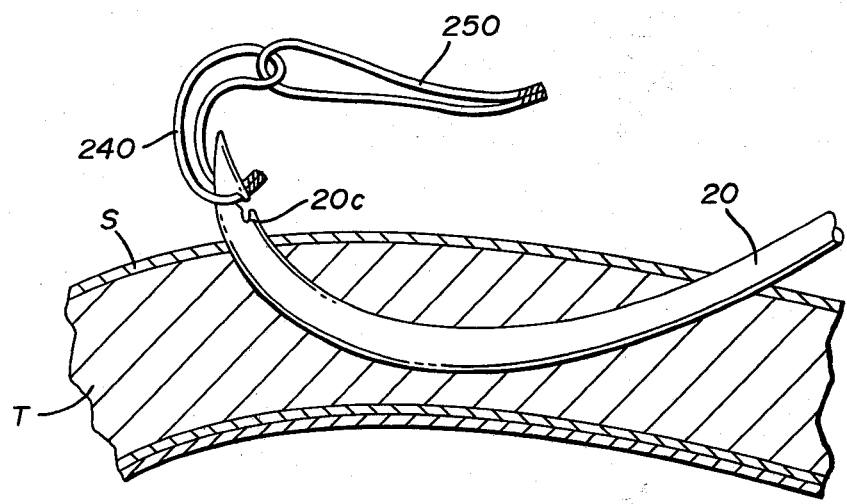
FIG. 32 is a cross-sectional view showing the reciprocal action of that in FIG. 31 in which a second loop of a preformed unit is received in a backwardly inclined strand carrying pocket so that the preformed unit is drawn into the scalp as the skewer is withdrawn.
Figure 33:
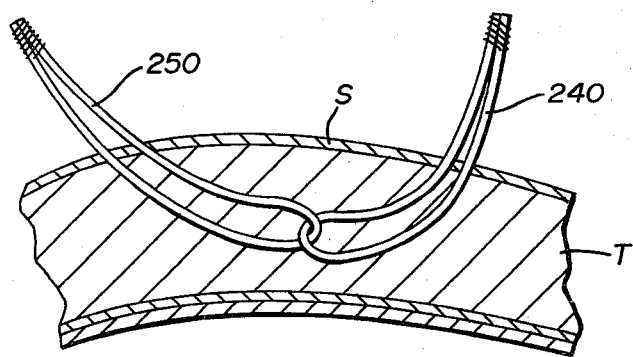
FIG. 33 is a cross-sectional view with the skewer removed and the joined loops of the strands or fibers placed at the lowest depth of the pathway created by the skewer.

Referring then to FIGS. 31, 32 and 33, the method of employing the "unit" of FIGS. 26 through 30 is illustrated.

For example, in FIG. 31, it will be noted that the skewer 20, which is similar to the skewer illustrated in FIG. 2 of the drawings, has a pocket 20c at one end. One of the loops 250 is engaged in the socket and the skewer is passed from the right to the left of FIG. 31 through the scalp and through the subcutaneous tissue T. The skewer can be passed completely through so that its end projects beyond the scalp and the loop 250 can then be disengaged. Withdrawal of the skewer will leave the two strands in place with their point of engagement being located at the bottom most point of the passageway formed by the skewer 20. The free ends will project above the scalp, and all that is necessary at that point is to sever the free ends adjacent their point of engagement so that the ends will truly be free and will be capable of simulating the natural hair.

It should be noted at this point that it is important to sever these ends otherwise during grooming a comb would tend to lodge in the loops formed and dislodge the replacement hair.

FIG. 32 shows a modified method of operation wherein the skewer 20 is first passed through the scalp and tissue and the loops 240 and 250 are engaged by the notch 20c. At this time it is merely necessary to withdraw the skewer 20 to the right of FIG. 32 until the strands are located as illustrated in FIG. 33 following which the skewer can be removed keeping in mind, of course, that the projecting joined ends should then be removed or severed.

Figure 34:
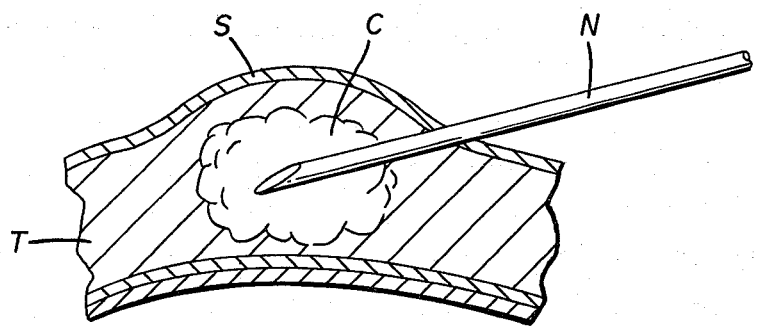
FIG. 34 is a cross-sectional view showing the method of producing a wheal with a needle and syringe.
Figure 35:
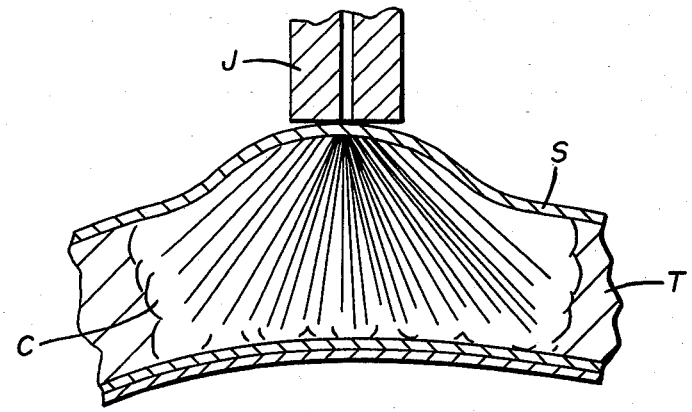
FIG. 35 is a cross-sectional view similar to FIG. 34 showing the production of a wheal using a jet injector.

FIGS. 34 and 35 disclose means for providing a "wheal". It may be recalled that FIG. 23 shows such a wheal formed by merely physically pinching the scalp and tissue to form a raised area. It has been found that such a transient wheal can be formed by injecting a local anesthetic or other chemical agent C by means of a needle N (FIG. 34) or by injecting the agent C by means of the jet injector device J (FIG. 35) either of these methods causes the scalp S and tissue T to swell thus producing the circumscribed area of the transient wheal. This makes the use of a skewer much easier and more effective and permits deeper implacement of the "unit". Of course, forming the wheal in this fashion could also be employed in connection with the method illustrated in FIGS. 12 through 25.

Thus, by the methods disclosed it will be seen that the strands are securely interlocked or engaged beneath the surface of the scalp to resist removal and separation. It will also be noted that the biodegradable tissue adhesive or tissue inert materials chemically assist in the retention process both at the interlock or interengagement point and at the puncture points.

It will also be noted that the cellular adaption from natural healing around and about the fibers or strands in the tissue beneath the scalp will further aid in their retention.

While a full and complete description of the invention has been set forth in accordance with the dictates of the Patent Statutes it should be understood that modifications can be resorted to without departing from the spirit hereof or the scope of the appended claims.

Thus it should be noted that certain tissue adhesive compositions or tissue inert materials have been referred to but it should be understood that the invention is not intended to be limited to any specific formulation. It is contemplated that any compound which is not tissue toxic and which has the characteristics of being a tissue adhesive, biodegradable, antibacterial and having hemostatic or tissue inert properties will be suitable.

What is claimed is:

1. A method of securing replacement strands of hair to the head of a human being comprising the steps of:
   (A) forming at least a first strand of hair into a U-shaped loop;
   (B) penetrating the scalp and passing said first strand through the scalp tissue so that the base of the loop and the open ends thereof project beyond the surface of the scalp;
   (C) forming at least a second strand of hair into a U-shaped loop;
   (D) interengaging said first and second strands;
   (E) forming a third strand of hair into a U-shaped loop;
   (F) passing said third strand through the scalp tissue so that the base of the loop and the open ends thereof project beyond the surface of the scalp in opposed relation to the base and open ends of said first strand;
   (G) forming a fourth strand of hair into a U-shaped loop;
   (H) interengaging said third and fourth strands;
   (I) pulling said first and second and said third and fourth strands in opposite directions until the interengaged portions thereof are disposed beneath the surface of the scalp with the open ends thereof projecting above the surface of the scalp.

2. The method of claim 1 further characterized by the step of bonding said first and second strands and said third and fourth together at their area of engagement with a biodegradable tissue adhesive prior to step I.

3. The method of claim 1 further characterized by the step of sealing the points of penetration of the scalp with a biodegradable tissue adhesive and hemostatic agent.

4. The method of claim 1 wherein said interengaged portions of said first and second strands and said third and fourth strands are drawn to approximately the midpoint of the channel formed during passage of said first strand.

* * * * *